United States Patent [19]

Iwamatsu et al.

[11] 4,151,041

[45] Apr. 24, 1979

[54] PROCESS FOR PRODUCTION OF MALTOPENTAOSE AND MALTOHEXAOSE

[75] Inventors: Katsuyoshi Iwamatsu, Kanagawa; Shoji Omoto, Tokyo; Takashi Shomura, Yokohama; Shigeharu Inoue, Yokohama; Taro Niida, Yokohama; Takashi Hisamatsu, Yokohama; Singo Uchida, Yokohama, all of Japan

[73] Assignee: Meiji Seika Kaisha, Ltd., Kyobashi, Japan

[21] Appl. No.: 826,762

[22] Filed: Aug. 22, 1977

[30] Foreign Application Priority Data

Aug. 23, 1976 [JP] Japan .................................. 51-99756

[51] Int. Cl.$^2$ .......................... C12D 13/02; C12B 1/00
[52] U.S. Cl. .................................. 195/31 P; 195/80 R
[58] Field of Search .................... 195/31 R, 80 R, 96

[56] References Cited

U.S. PATENT DOCUMENTS 4,039,383  8/1977  Pankratz ............................ 195/31 R

OTHER PUBLICATIONS

Omoto et al., "Studies on a New Antibiotic SF-1130. II, Isolation and Physio Chemical Properties of SF-1130." Chem. Abstracts, vol. 84, No. 21, p. 101 (1976), abs. No. 145351j.

Omoto et al., "Antiobiotic SF-1130 from Streptomyces," Chem. Abstracts, vol. 80, No. 15, p. 248 (1974), Abs. No. 81046w.

*Primary Examiner*—Thomas G. Wiseman
*Attorney, Agent, or Firm*—Haight & Huard

[57] ABSTRACT

Maltopentaose and maltohexaose are produced with commercial advantage by cultivation of *Streptomyces myxogenes* SF-1130 strain under aerobic conditions in an appropriate culture medium and recovery from the resultant culture.

3 Claims, 1 Drawing Figure

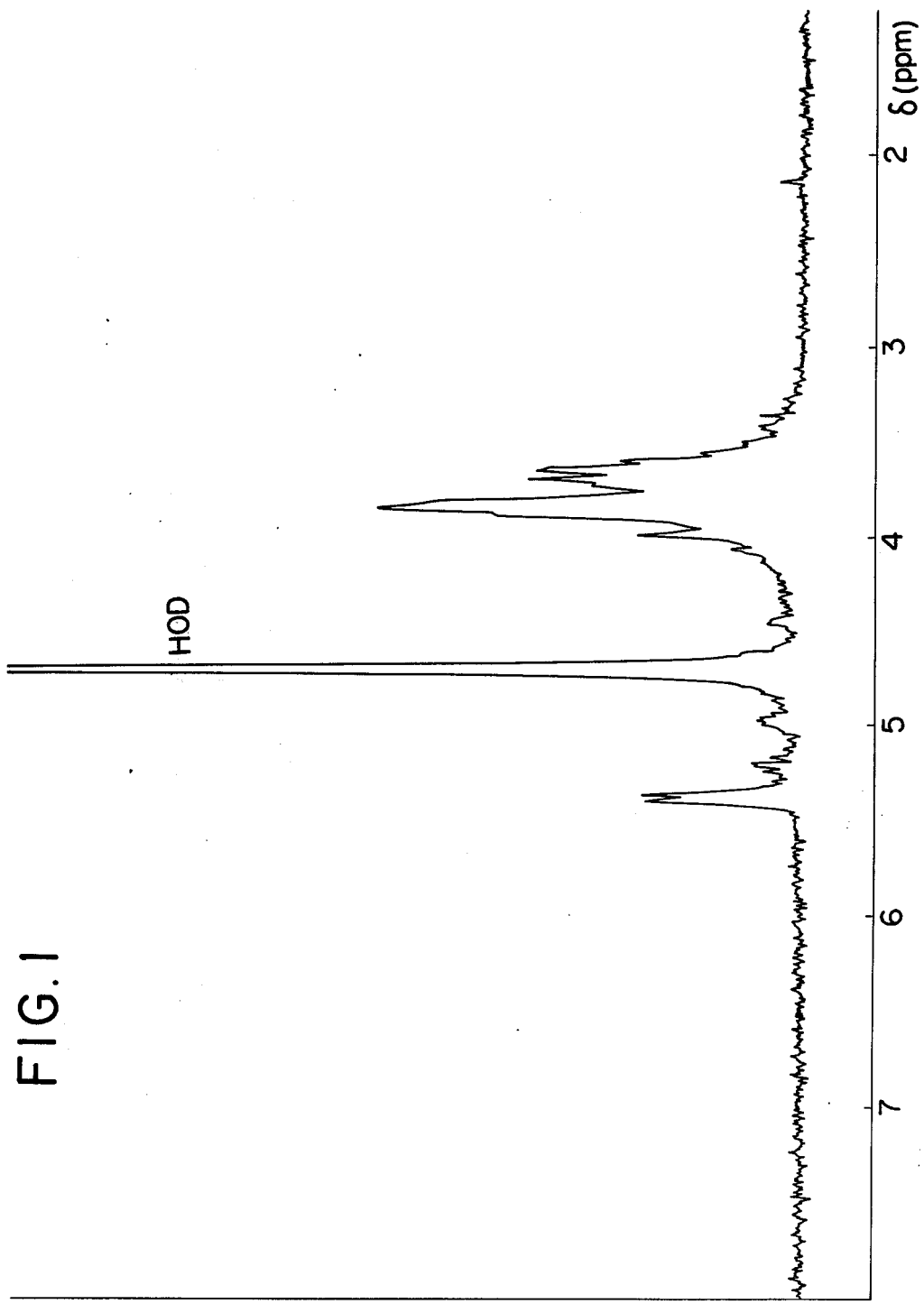

PROCESS FOR PRODUCTION OF MALTOPENTAOSE AND MALTOHEXAOSE

BACKGROUND OF THE INVENTION

1. Field of the Invention

This invention relates to a process for the production of maltopentaose and maltohexaose by cultivation of a microorganism belonging to the genus Streptomyces.

2. Description of the Prior Art

Known methods of producing maltopentaose and maltohexaose include isolation from a corn syrup (R. L. Wistler et al, J. Am. Chem. Soc. 77, (1951) p 5761) or acid hydrolysis of starch (W. J. Whelan et al, J. Chem. Soc. (1953) P 1293) or treatment of starch with an amylase isolated from fermentation broths of bacteria and fungi or from digestive juices of animals (Kainuma et al, FEBS Letters, 26, (1972) P 281). These methods have some disadvantages of poor yields of maltopentaose and maltohexaose or of troublesome operation for isolating the amylase to be used, and hence they are less applicable for large production of maltopentaose and maltohexaose on a commercial scale.

SUMMARY OF THE INVENTION

In these circumstances, we have studied and searched for a commercially advantageous process for the production of maltopentaose and maltohexaose and, as a result, we have now found that these substances can be isolated directly from the fermentation broth in which a certain strain of the genus Streptomyces has been incubated aerobically.

DETAILED DESCRIPTION OF THE INVENTION

According to this invention, therefore, there is provided a process for the production of maltopentaose and/or maltohexaose which comprises cultivating a strain of the genus Streptomyces capable of producing maltopentaose and/or maltohexaose under aerobic conditions in a culture medium containing nutrient sources for a period of time sufficient to produce and accumulate maltopentaose and/or maltohexaose in the culture, and recovering the substance(s) thus produced from the culture.

We have further found that maltopentaose and maltohexaose, which possess no in vitro antimicrobial activity in themselves, have a beneficial effect of increasing the host-defense activity against infection, or adjuvant effect to the immuno-potentiating and antibacterial activities of new antibiotics, SF-1130 $X_1$ and $X_2$ substances which have been described and claimed in our pending Japanese Patent Application No. 99757/76.

In carrying out the process of this invention, any strain of the genus Streptomyces may be used so long as it substantially produces maltopentaose and/or maltohexaose. A specific example of the strain which may be suitably used is an SF-1130 substance-producing strain which we have isolated from a soil sample and which we have designated as Streptomyces myxogenes SF-1130 strain (see Japanese Patent Publication No. 30393/73). This strain has been deposited in Japanese public depository "Fermentation Research Institute" under deposit number FERM-P 676 and also in the American Type Culture Collection, Rockville, Maryland, U.S.A., under ATCC number 31305. The SF-1130 Strain has the following microbiological characteristics:

1. Morphological observation

Substrate mycelia are well grown on various culture media, while the formation of aerial mycelia is generally poor. On starch agar and starch-yeast extract agar where aerial mycelia develop, short, dense aerial mycelia are formed from the substrate mycelia. The mycelia produce monopodially branches, no whorl-branching being observed.

The aerial mycelia bear at their tips spirals, most of which are of the compact closed type and some of which are of the incomplete or open type. No formation of sclerotium is observed. Electron-microscopic observation shows that the surface structure of the spores is smooth. The spores are of elliptical or cylindrical shape and have a size of 0.6–0.7×0.9–1.0 microns.

2. Cultural characteristics on various culture media are set out in Table 1 below:

Table 1

| Culture medium | Growth | Aerial mycelium | Soluble pigment |
|---|---|---|---|
| Sucrose-nitrate agar | Poor growth, colorless | Poor, white | None |
| Glucose-asparagine agar | Brown to greyish brown, reverse side faintly tinged with red color | None | None |
| Glycerol-asparagine agar | Brown | None | None |
| Calcium malate agar | Thin growth, pale brown | None | None |
| Glycerol-calcium malate agar | Brown | None | None |
| Starch agar (Inorganic Salts starch agar) | Pale brown to brown | Powdery, greyish brown, development mainly at periphery of colony | None |
| Oatmeal agar | Good, pale brown | Grey | None |
| Nutrient agar | Good growth with wrinkles, brown reverse side | None | Brown |
| Starch yeast-extract agar | Pale brown to brown | Greyish brown to Grey | Pale brown |
| Yeast extract-malt extract agar | Good, reddish brown | None | Brown |
| Tyrosine agar | Dark brown | None | Blackish brown |
| Potato plug | Raised growth with wrinkles, brown | None | Brown |
| Carrot plug | Greyish brown growth with wrinkles | None | Pale brown |
| Gelatin (20° C.) | Cream color | None | Dark brown to black |
| Skimmed milk (37° C.) | Bottom growth, pale brown | None | None |
| Loeffler's coagulated serum (37° C.) | Dark grey | None | None |
| Egg(37° C.) | Dark grey to dark brown | None | Grey pigment at periphery of the |

Table 1-continued

| Culture medium | Growth | Aerial mycelium | Soluble pigment |
|---|---|---|---|
| Glucose-Czapek's solution | Bottom growth, cream | None | growth None |
| Cellulose | No growth | — | — |

Note:
The incubation temperature was 28° C. unless otherwise indicated.

3. Physiological properties

| | | |
|---|---|---|
| Liquefaction of gelatin | : | Positive |
| Hydrolysis of starch | : | Positive |
| Production of tyrosinase | : | Positive |
| Production of hydrogen sulfide | : | Positive |
| Chromogenicity | : | Positive |
| Degradation of cellulose | : | Negative |
| Reduction of nitrate | : | Negative |
| Peptonization of skimmmed milk | : | Negative |
| Coagulation of skimmed milk | : | Negative |
| Dissolution of Loeffler's coagulated serum | : | Negative |

In addition to the above-mentioned physiological properties, the SF-1130 strain produces slime on agar medium and in a liquid medium, which is an important feature of the subject strain.

On an agar medium such as starch-yeast extract agar, starch agar or glucose-asparagine agar medium, it is observed that the slime is produced massively on the colony nearly 10 days after the incubation. It is also observed that when the SF-1130 strain is shake-cultivated in a liquid medium containing suitable carbon sources (glucose, starch, etc.) and nitrogen sources (yeast extract, soybean meal, wheat embryo etc.), then the culture broth gradually becomes viscous with formation of a slime.

4. Utilization of carbon sources (1) Utilized: xylose, glucose, galactose, maltose, sucrose, lactose, raffinose, dextrin, starch, glycerol, inositol, sodium acetate, sodium citrate and mannose.

(2) Doubtful: arabinose, fructose and salicin.

(3) Not utilized: rhamnose, inulin, dulcitol mannitol, sorbitol, sodium succinate and cellulose.

The aforesaid microbiological characteristics of the SF-1130 strain may be summarized as follows:

(1) The aerial mycelium forms closed spirals at its tip and the surface structure of the spore is smooth.

(2) The aerial mycelium, which is greyish brown to grey in color, is produced very poorly.

(3) The growth on synthetic culture media is brown to greyish brown in color.

(4) On organic culture media, chromogenicity is observed.

(5) Slime is produced on agar medium and liquid media.

In view of the microbiological characteristics described above, there may be mentioned *Streptomyces phaeochromogenes*, *Streptomyces purpureochromogenes* and *Streptomyces noboritoensis* as known strains related to the SF-1130 strain. However, the SF-1130 strain is not coincident with any of these known strains as illustrated below:

*Streptomyces phaeochromogenes* produces abundant aerial mycelia and forms brown soluble pigment on sucrose-Czapek's agar and calcium malate agar culture media, while the SF-1130 strain shows poor production of aerial mycelium and no formation of soluble pigment on said culture media.

Whilst *Streptomyces purpureochromogenes* produces orange to reddish orange colored growth on potato plug medium, forms no hydrogen sulfide and causes coagulation of skimmed milk, the SF-1130 strain produces brown growth on the same medium and causes formation of hydrogen sulfide but no coagulation of skimmed milk.

*Streptomyces noboritoensis* forms no spiral and produces green soluble pigment on starch agar medium (the production of green soluble pigment is not mentioned in the prior art, but, in fact, has been appreciably observed for this type strain), whereas the SF-1130 strain forms spirals but produces no soluble pigment on starch-synthetic agar. Moreover, the SF-1130 strain is distinguishable from *Streptomyces noboritoensis* also in utilization of mannitol and sucrose.

Thus, the SF-1130 strain is clearly differentiated from any of the known related species of the genus Streptomyces. The SF-1130 strain is further distinctive from any known species of Streptomyces in that the former exhibits the peculiar properties of producing slime as already stated, while the latter produces no slime according to the prior art.

In consequence, the SF-1130 strain has been identified as a new species of the genus Streptomyces and designated as "*Streptomyces myxogenes* SF-1130".

The SF-1130 strain has properties which are liable to vary as may be usually observed with other species of Streptomyces. Thus, for example, the SF-1130 strain may produce variants or mutants when treated with various mutagens such as ultraviolet rays, X-rays, high-frequency electromagnetic waves, radioactive rays and chemicals. Any natural or artificial variant or mutant of the SF-1130 strain may be used in the process of this invention, so long as it has the ability to produce maltopentaose and/or maltohexaose.

In the process of this invention, the strain for present use may be cultivated in a manner known per se in a culture medium containing nutrient sources which are assimilable by ordinary microorganisms. For this purpose, use may be made of any known nutrient which has been generally employed in the cultivation of known strains of Streptomyces. Examples of the nutrient sources to be used include glucose, starch, maltose syrup and molasses as carbon sources; and soybean meal, wheat embryo, dried yeast, peptone, meat extract, corn steep liquor, ammonium sulfate and sodium nitrate as nitrogen sources. If required, inorganic salts such as calcium carbonate, sodium chloride, potassium chloride, phosphates and the like may be added. In addition, such organic and inorganic materials as to aid the growth of the strain used and to promote the production of maltopentaose and/or maltohexaose may be incorporated in the culture medium.

As the cultivation method which can be employed in this invention, liquid cultivation, particularly under submerged aerobic conditions, is preferred as is generally used in the production of antibiotics. The cultivation is conducted under aerobic conditions, suitably at a temperature of 25° to 38° C. and most frequently at a temperature in the vicinity of 28° C. Under these circumstances, the production of maltopentaose and/or maltohexaose in the culture broth reaches a maximum after either shake-cultivation or tank-cultivation during a period of 2 to 5 days.

Both maltopentaose and maltohexaose, which fall within the category of oligo-saccharides of neutral nature as mentioned hereinafter, exhibit no in vitro antimicrobial activity in themselves but have the physio-chemical characteristics set out hereinbelow. By taking advantage of the physio-chemical characteristics, these substances can be recovered from the culture broth in which they have been produced and accumulated.

For instance, the maltopentaose and maltohexaose produced by the cultivation of the SF-1130 strain can be recovered from the culture broth by the following procedure: The culture broth is filtered under acidic conditions to remove the mycelia and insoluble matter, and the broth filtrate is passed at pH 3 through a column of a strongly acidic ion-exchange resin, for example, Dowex 50 W × 2 (a product made by Dow Chemical Co., U.S.A.) to separate basic substances dissolved in the broth filtrate, followed by passage through a column of active carbon to adsorb the maltopentaose and maltohexaose on the active carbon. The carbon column is then washed with water and eluted successively with aqueous solutions containing ethanol at concentrations increasing stepwise from 10% to 15%, 20% and 25%. Each of the eluates is collected in fractions and subjected to paper chromatography developed with a solvent consisting of n-butanol-pyridine-water-acetic acid (6:4:3:1 by volume). Those fractions which give a single spot at R raffinose value = 0.25 (calculated as assumed that raffinose gives a Rf value of 1.00; hereinafter referred to as R raffinose) are combined together and concentrated to dryness to afford maltohexaose in the form of a colorless powder. Those fractions which give a single spot at R raffinose = 0.41 are combined together and concentrated to dryness to afford a colorless powder of maltopentaose.

A similar procedure where the paper chromatography is replaced by column chromatography on cellulose using a developing solvent of n-butanol-pyridine-water-acetic acid (6:4:3:1 by volume) also enables the maltopentaose and maltohexaose to be recovered from the culture broth. If necessary, the substances thus recovered may be further purified by dissolution in water and addition of ethanol for re-precipitation.

The proportion of maltopentaose and maltohexaose produced by the cultivation of the SF-1130 strain depends on the culture conditions, although a predominant proportion of maltopentaose is generally produced.

When the SF-1130 strain is cultivated according to the process of this invention, in addition to the desired substances maltopentaose and maltohexaose, SF-1130 $-x_1$ and $-x_2$ substances (either one or both of these substances is or are generically denoted as SF-1130 $-x$ substance) as the new compounds are also produced and accumulated in the culture broth. The SF-1130-x substance is a weakly basic oligosaccharide which exhibits an antibacterial activity and which is readily soluble in water, hardly soluble in methanol and ethanol but insoluble in acetone. On the other hand, both maltopentaose and maltohexaose are neutral oligosaccharides which possess no in vitro antibacterial activity in themselves and which are readily soluble in water but insoluble in ethanol and acetone. The desired substances of this invention can be separated from the SF-1130 $-x$ substance due to the difference in their properties as stated above. Thus, for example, if the filtrate obtained by filtering the acidified culture broth from the cultivation of the SF-1130 strain is passed through a column of strongly acidic ion-exchange resin, then the SF-1130$-x$ substance contained in the filtrate is adsorbed on said resin but the maltopentaose and maltohexaose are not adsorbed thereon. The effluent from the column containing the latter two is then passed through a column of active carbon to adsorb them on the active carbon. The carbon column is washed with water and eluted successively with aqueous solutions containing ethanol at different concentrations in the range 10 to 25%, when the maltopentaose and maltohexaose are eluted out in sequence. Then, fractions containing solely maltopentaose and the fractions containing solely maltohexaose are collected separately from each other due to difference in the elution sequence of these substances.

According to a preferred embodiment of the process of the present invention, therefore, there is provided a process comprising the successive steps of cultivating *Streptomyces myxogenes* SF-1130 under aerobic conditions in a culture medium containing assimilable carbon and nitrogen sources at a temperature of 25°–38° C., filtering the culture broth under acidic conditions, passing the filtrate through a column of strongly acidic ion-exchange resin, passing the effluent through a column of active carbon, washing the carbon column with water, followed by elution successively with aqueous solutions containing ethanol at different concentrations, collecting the given fractions of the eluates, concentrating said fractions to dryness to afford a crude powder comprising a mixture of maltopentaose and maltohexaose, passing the crude power taken up in water through a column of active carbon which is then washed with water and eluted with aqueous solutions of ethanol, collecting the eluates in fractions, subjecting the fractions to paper chromatography developing with a mixed solvent of n-butanol-pyridine-acetic acid-water, collecting the fractions which give a single spot characteristic of maltopentaose, followed by concentration to dryness to yield maltopentaose in the form of colorless pure powder and collecting the further fractions which give a single spot characteristic of maltohexaose, followed by concentration to dryness to yield maltohexaose also in the form of colorless pure powder.

The maltopentaose and maltohexaose produced by the present invention have the physio-chemical properties shown in Table 2 below:

Table 2

| Properties | Maltopentaose | Maltohexaose |
|---|---|---|
| Appearance | Colorless, amorphous powder | Colorless, amorphous powder |
| Melting point | 190° C.(decomp.) | 186° C.(decomp.) |
| Elemental analysis | | |
| Found. | C, 41.3 ; H, 7.2 | C, 43.48 ; H, 6.30 |
| Calcd. | C, 40.8 ; H, 6.62 | C. 43.63 ; H, 6.31 |
| (Molecular formula) | ($C_{30}H_{52}O_{26}.3H_2O$) | ($C_{36}H_{62}O_{31}$) |
| Molecular weight (measured by mass spectrometry for completely methylated product) | 1066 | 1270 |
| Specific rotation | +134° (c.=1 in water) | +169° (c.=1 in water) |

Referring to the attached drawing:

FIG. 1 shows a nuclear magnetic resonance absorption spectrum of the maltopentaose produced by the present invention.

In further experiments each of the substances produced by the invention was heated in 1 N sulfuric acid at 100° C. for 5 to 6 hours and the product was subjected to paper chromatography using a developer of n-butanol-pyridine-acetic acid-water (6:4:1:3 by volume) to give a single spot in each case, which was identical to that of glucose. In the same paper chromatography of the products enzymatically degraded with $\beta$-amylase, the degraded product of the maltopentaose gave two spots of maltose and maltotriose and the degraded product of the maltohexaose gave only a single spot of maltose.

In view of the foregoing, it is evident that the desired substances of this invention are identified as maltopentaose and maltohexaose being oligosaccharides of neutral character.

A cellular immunity test according to the delayed skin reaction technique concerning mice infected with ascites tumor of "Sarcoma 180" has shown that both maltopentaose and maltohexaose have an adjuvant effect of increasing the immuno-potentiating activity exhibited by the SF-1130—x substance.

The test was carried out by the following procedure: A group of ICR-JCL mice (male) having an average body weight of 31.58±4g (8 weeks old) (six mice per group) were inoculated with ascites tumor of "Sarcoma 180". 24 hours after the inoculation of the tumor cells, each of the drug samples to be tested was subcutaneously administered once into the mice. Two days after the inoculation an ethanolic solution of 5% picryl chloride was applied to the hair-shaved abdomens of mice to establish the sensitization. Subsequently, each drug sample under test was subcutaneously administered once a day for four successive days. Nine days after the inoculation, a solution of 1% picryl chloride in olive oil was applied to the two sides of both ears of mice to establish the secondary sensitization. 24 hours after the secondary sensitization, the degree (%) of increase in thickness of the ears was evaluated for the test mice. The extent of the delayed skin reaction can be assessed from the percentage increase.

The test results are set out in Table 3 below.

Table 3

| Drug sample administered | Dosage (mg/kg body) | Degree of increase in thickness ($\times 10^{-3}$ cm) | Percentage increase (%) |
|---|---|---|---|
| SF-1130-x* + maltohexaose | 100 + 200 | 7.3 ± 1.530 | 135.2 |
| SF-1130-x* + maltopentaose | 100 + 200 | 7.0 ± 1.240 | 129.6 |
| SF-1130-x* | 100 | 6.3 ± 2.890 | 116.7 |
| Maltohexaose | 200 | 4.7 ± 0.988 | 87.0 |
| Control (No treatment) | — | 5.4 ± 1.136 | 100.0 |

*SF-1130-x substance, referred to herein, is a mixture of the SF-1130-$x_1$ substance, and -$x_2$ substance as already stated.

Further testing has shown that both maltopentaose and maltohexaose, which exhibit no in vitro antimicrobial activity in themselves, have an effect of improving the antibacterial activity of the SF-1130—x substance.

The test was conducted by a conventional paper disc-plate method. Thus, the SF-1130—$x_2$ substance was dissolved in distilled water at a concentration of 1 mg/cc or 2 mg/cc, and with the test solutions so prepared were impregnated paper discs made of filter paper 8 mm in diameter which were subsequently air-dried. These paper discs were placed on an upper plate layer of the known mycin-assay incubation medium comprising 0.5% peptone, 0.3% meat extract and 1.5% agar (pH 6) which contained the test microorganism to be incubated therein and which was laid over the lower layer of agar medium in the assaying dish. The incubation was made at a temperature of 37° C. overnight, and subsequently the diameters of the inhibition zones formed around the paper discs were measured. The test results so obtained are shown in Table 4 below. These tests were repeated in the same manner as above but with the additional incorporation of 1.25 mg/cc of maltopentaose or maltohexaose into the upper plate layer of the micin-assay incubation medium. The test results so obtained are also shown in Table 4, from which we have discovered that the additional presence of maltopentaose or maltohexaose improves the antibacterial activity of the SF-1130—$x_2$ substance. In similar tests, we have further found that when maltopentaose or maltohexaose is used in combination with the SF-1130-$x_1$ substance, the former generally improves the antibacterial activity of the latter, too, with an exception that improvement in the antibacterial activity is not observed against *Klebsiella pneumoniae*. Control testing was also conducted in which the antibacterial potency of the SF-1130-$x_2$ substance alone was estimated in the absence of maltopentaose or maltohexaose. All the results of the tests conducted in this respect are shown in Table 4.

Table 4

| | Diameter of Inhibition Zone (mm) | | | | | |
|---|---|---|---|---|---|---|
| | Control | | Addition of maltopentaose | | Addition of maltohexaose | |
| Test microorganism | Level of SF-1130-$x_2$ | | Level of SF-1130-$x_2$ | | Level of SF-1130-$x_2$ | |
| | 2mg/cc | 1mg/cc | 2mg/cc | 1mg/cc | 2mg/cc | 1mg/cc |
| *Escherichia coli* K-12R | 16.0 | 12.0 | 26.0 | 24.1 | 26.2 | 24.3 |
| *Escherichia coli* (resistant to chloroamphenical | 14.7 | 13.5 | 23.9 | 21.0 | 24.0 | 21.1 |
| *Shigella sonnei* | 13.0 | Small | 20.1 | 18.2 | 20.0 | 18.1 |
| *Proteus vulgaris* | Small | 0 | 16.0 | 12.7 | 16.4 | 13.0 |
| *Salmonella typhi* | 13.8 | 12.1 | 19.8 | 18.0 | 19.7 | 17.9 |

It is to be noted that no antibacterial activity of maltohexaose and maltopentaose in themselves has been observed under the above testing conditions.

Still further testing has shown that both maltopentaose and maltohexaose may stimulate the host-defense system in living animals against bacterial infection.

The test was conducted as follows: The crude, yellowish brown powder obtained in Example 1 was reprecipitated from water-ethanol and the reprecipitate was dissolved in a phosphate-buffered saline at ph 7.2. The resultant solution containing a mixture of maltopentaose and maltohexaose was intraperitoneally administered into a group of JCL-ICR mice (male) having an average body weight of 20g (4 weeks old) (eight mice per group) at a dosage of 100 mg/kg body or 20 mg/kg body. The administration was effected three times at an interval of 48 hours.

72 hours after the final administration, the mice were intraperitoneally inoculated with 0.5 ml/mouse of a cell dispersion of *Staphylococcus aureus* Smith S-424 strain which had been prepared by dilution of the incubated culture with physiological saline solution followed by addition of 5% mucin. The number of the mice that survived was counted during five days after the inoculation and the $LD_{50}$ value of the bacterial cells (the number of the bacterial cells necessary to kill 50% of mice) calculated in each case. Control testing was also conducted where the treatment with the mixture of maltopentaose and maltohexaose was omitted.

The test results are set out in Table 5 below. It is found that the mixture of maltopentaose and maltohexaose gives rise to an increase in the $LD_{50}$ value (viz. preventative effect) by approx. 42.9 times at a dosage of 100mg/kg and by approx. 6.2 times at a dosage of 20mg/kg.

Table 5

| Dosage of test mixture | Survival of mice at various doses of bacteria inoculated (cells/mouse) | | | | $LD_{50}$ of bacteria cells |
| --- | --- | --- | --- | --- | --- |
| | $9.3 \times 10^7$ | $1.9 \times 10^7$ | $3.7 \times 10^6$ | $7.4 \times 10^5$ | |
| 100 mg/kg | 3/8 | 6/8 | 8/8 | 8/8 | $9.0 \times 10^7$ |
| 200 mg/kg | 1/8 | 3/8 | 8/8 | 8/8 | $1.3 \times 10^7$ |
| Control | — | 0/8 | 2/8 | 8/8 | $2.1 \times 10^6$ |

This invention is further illustrated but not limited by the following Examples.

EXAMPLE 1

The strain *Streptomyces myxogenes* SF-1130 (identified as FERM-P.676 or ATCC 31305) was inoculated to 20l of a liquid culture medium (pH 7.0) comprising 5.0% maltose syrup, 2.5% soybean meal, 1.0% wheat embryo and 0.25% sodium chloride. The inoculated medium was incubated under aeration and agitation at 28° C. for 66 hours in a jar-fermenter. At the end of the incubation, the resultant culture broth was filtered under acidic conditions (pH 3) to give 15l of a broth filtrate.

The filtrate was passed through a column of 2l of a strongly acidic ion-exchange resin (Dowex 50 W × 2 made by Dow Chemical Co., U.S.A.) and the effluent from the column was then passed through a column (8 × 50 cm) of 2.5l of active carbon (made by Wako Junyaku K.K., Japan). The carbon column was well washed with water and eluted successively with aqueous solutions of 10%, 15%, 20%, 25% and 30% ethanol. The fractions (10l) obtained from the elution with the 20% and 25% ethanolic equeous solutions were concentrated to dryness to give 20g of a mixture of crude maltopentaose and maltohexaose in the form of yellowish brown powder.

15g of the powder was dissolved in 100 ml of water and the solution was passed through a column (4.0 × 33cm) of 350 ml of active carbon (made by Waco K.K., Japan) to adsorb the desired substances on the active carbon. The column was well washed with water, followed by elution successively with aqueous solutions of 10%, 15%, 20% and 25% ethanol. The eluate was collected in 15 ml-fractions and each of the fractions was subjected to paper chromatography developed with a mixed solvent of n-buthanol-pyridine-acetic acid-water (6:4:1:3 by volume). The fraction Nos. 261-340 which gave a single spot at R raffinose = 0.41 (calculated with assumption that the Rf value of raffinose is 1.00) colored by a reagent of silver nitrate were combined together and concentrated to dryness to yield 5.2g of colorless powder of maltopentaose. This powder was dissolved in 20 ml of water and the solution was filtered. 180 ml of ethanol was slowly added to the filtrate to re-precipitate the product, affording 4.8g of pure maltopentaose as colorless powder.

On the other hand, the fraction Nos. 396-500 which gave a single spot at R raffinose = 0.25 were treated by the procedure as described above to give 3.1g of pure maltohexaose as colorless powder.

EXAMPLE 2

4.0g of the crude, yellowish brown powder obtained in Example 1 was taken up in a small amount of water, adsorbed on a small proportion of cellulose powder and dried. The dried powder was placed on a column (4.5 × 18cm) of 300g of cellulose and developed with a mixed solvent of n-butanol-pyridine-acetic acid-water (6:4:1:3 by volume). The eluate was collected in 12ml-fractions, and each of the fractions subjected to paper chromatography using said mixed solvent as a developer. The fraction Nos. 143-224 which gave a single spot at R raffinose=0.41 colored by a reagent of silver nitrate were combined together and treated as in Example 1 to yield 1.05g of a colorless powder of maltopentaose.

The fraction Nos. 250-345 giving a single spot at R raffinose = 0.25 were similarly treated to yield 740 mg of a colorless powder of maltohexaose.

What we claim is:

1. A process for the production of a saccharide selected from the group consisting of maltopentaose, maltohexaose, and mixtures thereof which comprises cultivating a microorganism having the identifying characteristics of Streptomyces myxogens SF1130 under aerobic conditions in a culture medium containing nutrient sources for a time sufficient to produce and accumulate said saccharide, and recovering said saccharide.

2. A process according to claim 1, in which the microorganism is *Streptomyces myxogenes* SF-1130 strain (identified as FERM-P 676 or ATCC 31305) and is aerobically cultivated at a temperature of 25–38° C.

3. A process according to claim 2, comprising recovering the saccharide by filtering the culture broth under acidic conditions, passing the filtrate through a column of strongly acidic ion-exchange resin, passing the effluent through a column of an active carbon, washing the carbon column with water, followed by eluting successively with aqueous solutions containing ethanol at different concentrations, collecting the given fractions of the eluates, concentrating said fractions to dryness to afford a crude powder comprising a mixture of maltopentaose and maltohexaose, passing the crude power taken up in water through a column of active carbon which is then washed with water and eluted with aqueous solutions of ethanol, collecting the eluates in fractions, subjecting the fractions to paper chromatography developing with a mixed solvent of n-butanol-pyridine-acetic acid-water, collecting the fractions which give a single spot characteristic of maltopentaose, followed by concentrating to dryness to yield maltopentaose in the form of a colorless pure powder and collecting the further fractions which give a single spot characteristic of maltohexaose, followed by concentrating to dryness to yield maltohexaose also in the form of a colorless pure powder.

* * * * *